United States Patent [19]

Elmaleh et al.

[11] Patent Number: 4,524,059
[45] Date of Patent: Jun. 18, 1985

[54] FATTY ACID ANALOGS

[75] Inventors: David R. Elmaleh, Newton Center; Eli Livni, Brookline, both of Mass.

[73] Assignee: The General Hospital Corporation, Boston, Mass.

[21] Appl. No.: 461,734

[22] Filed: Jan. 28, 1983

[51] Int. Cl.$^3$ .................... A61K 49/00; A61K 43/00
[52] U.S. Cl. ........................................ 424/1.1; 424/9; 260/413
[58] Field of Search ...................... 424/1.1, 9; 260/413

[56] References Cited

U.S. PATENT DOCUMENTS 4,290,965 10/1981 Stocklin et al. ...................... 260/408
4,323,547  4/1982 Knust et al. ............................ 424/1

OTHER PUBLICATIONS

Elbenhut, Int. J. Appl. Rad. Isot., 33(1982) 499–504.
Metzler, David E., *Biochemistry*, (1977) p. 520.
Stewart et al., "Oral Hypoglycemic Agents", Campbell, Ed., Academic Press, New York (1969) p. 347.
Tutwiler, Experientia 29: (1973) p. 1340.
Tutwiler et al., Methods Enzymol. 72: (1981) p. 533.

*Primary Examiner*—Christine M. Nucker

[57] ABSTRACT

In one aspect, a radioactively labeled analog of a fatty acid which is capable of being taken up by mammalian tissue and which exhibits an in vivo beta-oxidation rate below that with a corresponding radioactively labeled fatty acid.

44 Claims, No Drawings

FATTY ACID ANALOGS

The government has rights to this invention pursuant to a grant or award from the Department of Energy.

BACKGROUND OF THE INVENTION

This invention relates to the diagnostic use of labeled fatty acids and to the treatment of diabetes.

Attempts have been made to monitor heart disease by injecting into a patient a radioactive fatty acid which is taken up by the heart, and then detecting the labeled fatty acid; e.g., by carrying out positron or photon tomography to produce images of the patient's heart. Such procedures are described in, e.g., Stöcklin U.S. Pat. No. 4,290,965 and Knust et al. U.S. Pat. No. 4,323,547.

Inhibitors of free fatty acid oxidation have been found to produce hypoglycemia in animals, as described in, e.g., Stewart et al. (1969) "Oral Hypoglycemic Agents," Campbell, Ed., Academic Press, New York, pg. 347; Tutwiler (1973) Experientia 29: 1340; and Tutwiler et al. (1981) Methods Enzymol. 72: 533.

SUMMARY OF THE INVENTION

In general, the invention features, in one aspect, a radioactively labeled analog of a fatty acid, the analog being capable of being taken up by mammalian tissue and exhibiting an in vivo beta-oxidation rate below that of the corresponding radioactively labeled fatty acid.

In preferred embodiments, the analog has a chain of six or more carbon atoms and has bonded to it, at the C3, C5, C7, or C9 position (counting from the carboxyl carbon atom; the carboxyl end of the molecule will hereinafter be referred to as the "right" end of the molecule, and the opposite end as the "left" end of the molecule), an organic substituent effective to lower the rate of in vivo beta-oxidation, the analog having at least three carbon atoms in the straight chain to the left of the carbon atom to which the substituent is bonded. Preferably the substituent causes the analog to be metabolically trapped in the tissue by permitting the first beta-oxidation step during which the carbon atom to which the substituent is bonded is beta to the carboxyl carbon to occur, while preventing the cleaving off from the analog of the two carbon atoms to the right of the carbon atom to which the substituent is bonded; most preferably that first step involves the bonding of coenzyme A to the carboxyl carbon atom and the cleaving is prevented by the blocking by the substituent of a beta-ketoacyl SCoA intermediate.

In other preferred embodiments, the radioactive label is $^{11}C$ in the carboxyl position, or is a radioactive isotope of a halogen which is bonded to a carbon atom on the straight chain, to an aryl group bonded to the omega-carbon atom of the chain, or to an aryl group bonded to the beta-carbon atom.

In another aspect, the invention features a fatty acid analog having a chain of six or more carbon atoms and a first organic substituent at the C3, C5, C7, or C9 position, this first substituent being effective to lower the beta-oxidation rate of the analog, the analog having at least three carbon atoms in the straight chain to the left of the carbon atom to which the first substituent is bonded, the analog also having a second organic substituent bonded to the antepenultimate carbon of the chain (the carbon atom on the chain 2 carbon atoms to the right of the omega-carbon), this second substituent being effective to lower the in vivo omega-oxidation rate of the analog.

In preferred embodiments, the second substituent is a methyl group, and the analog is radioactively labeled, or the analog is administered to a human patient in order to reduce the rate of the fatty acid metabolism of the patient.

In another aspect, the invention features a method of reducing the rate of fatty acid metabolism in a human patient comprising administering to the patient a fatty acid metabolism rate-lowering amount of the above di-substituted analog, or of the analog having just the first substituent.

In a preferred embodiment, the method is employed in the treatment of diabetes.

The analogs of the invention are selectively taken up by metabolizing tissue and are, because of their structure, metabolically trapped within the target organ, e.g., the patient's heart. This feature of the analogs allows the use of radioactively labeled analogs to obtain sequential images of the tissue over a long period of time. The analogs are not toxic and are safe for use with human patients.

The enzyme blocking activity of the analogs of the invention can depress the rate of fatty acid oxidation, improving muscle-glucose utilization in patients suffering from diabetes.

Other advantages and features of the invention will be apparent from the following description of the preferred embodiments thereof, and from the claims.

DESCRIPTION OF THE PREFERRED EMBODIMENTS STRUCTURE

The analogs of the invention are structurally identical to the corresponding fatty acids except for the presence of an organic substituent at the C3, C5, C7, or C9 position, and, in some embodiments, a second organic substituent bonded to the antepenultimate carbon of the chain or a radioactive label.

Any organic substituent of the analog should be small enough to permit the formation of the first chemical intermediate involved in the fatty acid beta- or omega-oxidation process; too large a substituent can alter the uptake and analogy behavior of the analog to an undesirably great extent. It is preferred that the substituent be an alkyl or heteroalkyl (alkyl containing one or more atoms other than hydrogen or carbon) group containing one to three carbon atoms, inclusive; an aryl or heteroaryl (aryl containing one or more atoms other than hydrogen or carbon) group having one or two aromatic rings each having six or fewer carbon atoms; or an aralkyl or heteroaralkyl group having one or two aromatic rings each having six or fewer carbon atoms and an alkyl group having one to three carbon atoms, inclusive.

The chemical nature, as well as the size, of any substituent can affect the properties of the analog. Generally, an analog having a substituent which does not render the analog excessively polar, e.g., an unsubstituted alkyl group, is taken up primarily by the heart, while an analog containing a polarizing group, e.g., an ether, or alcohol, will be taken up primarily by the liver.

The chain length of the analog also affects the tissue by which it is primarily taken up. Generally, a chain length of 12-20 carbon atoms, inclusive, is optimal for selective uptake by myocardial tissue, while a chain length of 5 to 11 carbon atoms inclusive will be preferred for selective uptake by the liver. The carbon chain of the analog can be saturated or unsaturated.

Preferred compounds of the invention are [1-$^{11}$C] beta-methylheptadecanoic acid, [1-$^{14}$C] beta-methylheptadecanoic acid, beta-methyl-omega (p-[$^{131}$I] iodophenyl) tetradecanoic acid, and beta-methyl-omega-(p-[$^{123}$I] iodophenyl) tetradecanoic acid.

Synthesis

According to one general method, the first step in the synthesis of beta-substituted analogs of the invention involves reducing a straight chain fatty acid having an organic substituent group bonded to the alpha-carbon atom, so that the acid group is converted to an alcohol. The alpha-substituted alcohol is then halogenated so that the hydroxyl group is replaced by a halogen atom. The next step is to substitute the halogen with a carboxylic acid group. This can be accomplished either by reacting the halogenated compound with carbon dioxide, e.g., in a Grignard reaction, or by carrying out an exchange reaction with the halogenated intermediate and sodium cyanide, followed by hydrolysis of the resulting nitrile. This step, if employing either carbon dioxide or sodium cyanide containing a radioactive isotope of carbon, labels the analog simultaneously with placing the substituent in the beta position. Alternatively, unlabeled carbon dioxide or sodium cyanide is used, so that an unlabeled fatty acid analog is made with the substituent at the beta-position. The unlabeled beta-substituted analog can then be radioactively labeled using any desired method, e.g., a positron emitting halogen isotope can be substituted in any position along the chain, using any conventional labeling technique.

According to a second general method, the first step in the synthesis of beta-substituted analogs of the invention involves replacing the hydroxyl group at the C1 position of a straight chain alcohol with a halogen atom. The halogenated compound is then converted into the corresponding organometallic compound which, when contacted with an omega-halogenated-beta-substituted ethyl ester, replaces the halogen on the ester, resulting in the formation of a straight chain beta-substituted ethyl ester, which is then cleaved at the ester linkage to yield ethanol and the desired beta-substituted fatty acid.

The synthesis of a fatty acid analog of the invention having an organic substitution at the C5, C7, or C9 position can be accomplished by selecting an appropriate alcohol and an appropriate omega-halogentated ethyl ester as starting materials in a variation of the second general method. For example, 2-nonanol and ethyl 4-iodo-butyrate can be employed in the synthesis of 5-methyldodecanoic acid; and 3-methyl-1-decanol and ethyl 4-iodo-butyrate can be employed in the synthesis of 7-methyltetradecanoic acid.

Similarly, an alcohol and an ester can be selected for the synthesis of an analog of the invention having both a substituent at the C3, C5, C7, or C9 position, and a second organic substituent bonded to the antepenultimate carbon of the chain. For example, 7-methyl-2-nonanol and ethyl 4-iodo-butyrate can be used to synthesize 5, 10-dimethyldodecanoic acid; and 8-methyl-1-decanol and ethyl 4-iodo-3-methyl-butyrate can be used to synthesize 3, 12-dimethyltetradecanoic acid.

The alcohol used in the second general method can have a phenyl group at the omega-position. In this case, the final product of synthesis can be labeled by replacing a hydrogen on the phenyl group with a radioactive halogen isotope.

In yet another variation of the second general method, the starting material can have a terminal carbon-to-carbon triple bond. In this case, the final product of synthesis can be reacted with catecholborane followed by treatment with radioactively labeled iodine monochloride to produce a radioactively labeled beta-substitited fatty acid analog with a terminal vinyl iodide group.

The synthesis of specific analogs of the invention will now be described.

[1-$^{11}$C] beta-methylheptadecanoic acid

[1-$^{11}$C] beta-methylheptadecanoic acid (BMHDA), is prepared in a 3-step process from 2-methylhexadecanoic acid, as follows.

First, 2-methylhexadecanol (II) is prepared by the reduction of 2-methylhexadecanoic acid (I) (commercially available) with lithium aluminum hydride, as follows, using standard procedures:

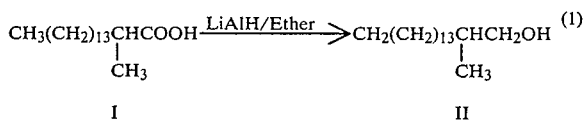

Thin layer chromatography of crude II shows the presence of very little starting material, and II is therefore used without further purification for the synthesis of 2-methyl-1-bromohexadecane (III):

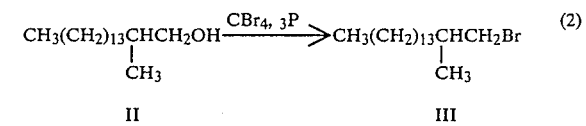

Reaction (2) is carried out according to the following modification of the procedure of Hooz and Gilani (1968) Can. J. Chem. 46: 86–87 for the preparation of alkyl bromides. First, triphenylphosphine (7.3 g, 28 mmol) and 2-methylhexadecanol (3.68 g, 14 mmol) are dissolved in 80 ml benzene. A solution of carbon tetrabromide (9.2 g, 28 mmol) in 20 ml benzene is added slowly and the mixture refluxed for 90 minutes. The reaction mixture is then cooled and filtered and the residue washed with 3×50 ml portions of petroleum ether. The residue is evaporated to dryness and then stirred with 100 ml petroleum ether and left overnight in a freezer. The solution is filtered, the residue washed with 2×25 ml petroleum ether, and the combined solution evaporated to dryness. Thin layer chromatography indicates the complete absence of starting material.

[1-$^{11}$C] beta-methylheptadecanoic acid (IV) is then prepared from III:

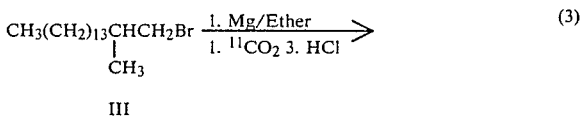

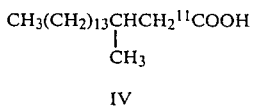

Reaction (3) is carried out as follows. A solution of III (300 mg, 0.94 mmol) in 5 ml ether (dried over CaH$_2$ and redistilled just before use) is injected into 5 ml refluxed ether containing magnesium (27 mg, 1.1 mmol). Refluxing is continued for 90 minutes under an argon atmosphere. The reaction mixture is cooled to room temperature and 1.5 ml of the solution is injected into a $^{11}$CO$_2$ trap and the solution shaken for 5 minutes. (The radiochemical yield is 35–40%.) The solution is then transferred to a separatory funnel, the trap is washed with 2×2 ml ether, and the combined ether solutions are shaken with 0.3 ml 1N HCl. The ether solution is washed twice with 2 ml water, dried using Na$_2$SO$_4$, and evaporated. The residue is dissolved in 4 ml propylene glycol and filtered through a 0.22 micron membrane filter. The radiochemical purity of the analog product, compound IV, as confirmed by tlc and HPLQ, is greater than 99%.

[1-$^{14}$C] beta-methylheptadecanoic acid

[1-$^{14}$C] beta-methylheptadecanoic acid is synthesized by a method substantially similar to the method outlined above for the synthesis of [1-$^{11}$C] beta-methylheptadecanoic acid. Instead of adding the radioactively labeled carbon in the form of labeled carbon dioxide as in reaction (3), $^{14}$C is preferably added to III in an exchange reaction with Na$^{14}$CN. Hydrolysis of the resulting nitrile yields the desired [1-$^{14}$C] beta-methylheptadecanoic acid.

Beta-methyl-omega-(p-[$^{131}$I] iodophenyl) tetradecanoic acid

Beta-methyl-omega-(p-[$^{131}$I]-phenyl) tetradecanoic acid (BMPTA) is synthesized in a four step process from 10-phenyl-1-decanol, as follows.

First, the hydroxyl group is halogenated:

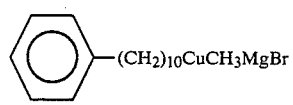
(4)

The resulting halogenated aralkane is then reacted with magnesium in tetrahydrofuran (THF) and with CH$_3$Cu(CH$_3$Li+CuI) to produce an organometallic intermediate:

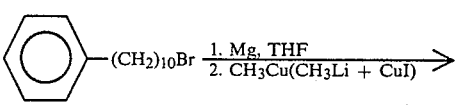
(5)

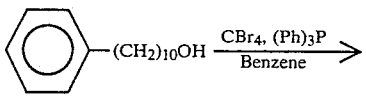

The organometallic intermediate of reaction (5) is then contacted with ethyl 4-iodo-3-methyl-butyrate to produce an ethyl ester:

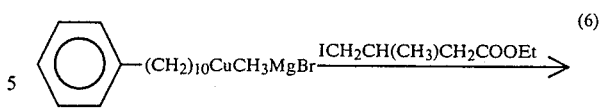
(6)

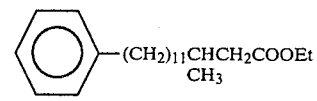

The ester of reaction (6) is then cleaved at the ester linkage to produce BMPTA:

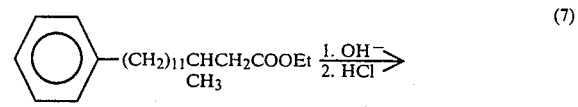
(7)

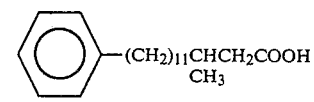

BMPTA is iodinated at the omega-phenyl position with $^{131}$I according to the method of Machulla et al. (1980) Eur. J. Nucl. Med. 5: 171–173.

To carry out the above synthesis, it is first necessary to synthesize the reactant used in reaction (6), ethyl 4-iodo-3-methyl-butyrate. This is accomplished in a three step process beginning with the conversion of 3-chloro-2-methyl propene into a Grignard reagent, which is then reacted with carbon dioxide, resulting in the addition of a carbon atom to the molecule:

$$CH_2=C(CH_3)CH_2Cl \xrightarrow[\text{2. CO}_2 \text{ 3. HCl}]{\text{1. Mg/Ether}} CH_2=C(CH_3)CH_2COOH \quad (8)$$

The resulting acid is reacted with ethanol to form the corresponding ethyl ester:

$$CH_2=C(CH_3)CH_2COOH \xrightarrow{\text{EtOH, H}^+} \quad (9)$$

$$CH_2=C(CH_3)CH_2COOEt$$

Iodine is then added across the double bond of the unsaturated ester product of reaction (9), resulting in the desired reactant, ethyl 4-iodo-3-methyl-butyrate:

$$CH_2=C(CH_3)CH_2COOEt \xrightarrow[\text{2. ICl}]{\text{1. B}_2\text{H}_6} \quad (10)$$

$$ICH_2CH(CH_3)CH_2COOEt$$

Beta-methyl-omega-(p-[$^{123}$I] iodophenyl) tetradecanoic acid

Beta-methyl-omega-(p-[$^{123}$I] iodophenyl) tetradecanoic acid is synthesized by a method substantially similar to the method outlined above for the synthesis of beta-methyl-omega-(p-[$^{131}$I] iodophenyl) tetradecanoic acid.

Use

[1-¹¹C] beta-methylheptadecanoic acid

[¹¹C] BMHDA is used to study myocardial metabolism in tissue distribution studies employing rats and mongrel dogs.

CD Fischer rats (175-225 g) are anesthetized with ether and 0.2 ml (2-10 Ci) of [¹¹C] BMHDA is injected through the femoral vein. The rats are sacrificed by ether asphyxiation at 5, 15, 30, and 60 minutes after dosing. The appropriate organs are excised and radioactivity measured in a NaI (T1) well scintillation counter. It is found that [¹¹C] BMHDA is selectively extracted by the heart muscle, and the radioactivity is retained in the heart for up to one hour. The lung activity is at all times lower than heart activity, and the liver activity increases during the course of the study.

Mongrel dogs are anesthetized with sodium pentabarbitol (Diabatol, 0.55 cc/kg) and 0.8-3 mCi of [¹¹C] MHDA is injected through a femoral vein. After 1 minute, serial blood samples are taken using a femoral vein catheter to determine the blood clearance rate. A 3 ml aliquot is taken every minute for the first 5 minutes, every 5 minutes for the next 15 minutes, and every 10 minutes for the next hour. The blood samples are weighed, counted in a well-scintillation counter, and the activity corrected for decay.

In order to determine the distribution over time of the [¹¹C] BMHDA in the heart and liver, 2-D images of the dogs are made using a positron camera. Prior to imaging, each dog is placed between the camera heads, a phantom filled with an aqueous solution of ⁶⁸Ga Cl₃ is placed beneath the animal, and transmission images taken. Sequential images are collected for 1 minute each at the following times: 3 minutes, 8 minutes, 13 minutes, 28 minutes, 48 minutes, and 60 minutes. The images are corrected for decay and for photon attenuation.

In a companion biodistribution study, uptake in 2 dogs in different areas of the myocardium and average uptake for the whole heart are determined. The highest regional uptake, as expected, is in the left ventricle.

Positron tomography images are obtained of the heart and liver of the 2 dogs 3, 13, and 48 minutes after injection with [¹¹C] BMHDA and the corresponding radioactively labeled fatty acid, [¹¹C] heptadecanoic acid (HDA). Into each dog there is injected, sequentially, [¹¹C] BMHDA and [¹¹C] HDA. Sequential images show that [¹¹C] HDA rapidly washes out of the tissue, in contrast with [¹¹C] BMHDA, which shows much higher retention in the myocardium: the radioactivity in the myocardium following injection of [¹¹C] BMHDA remains constant throughout the experiment (60 minutes).

In addition to its long retention time, [¹¹C] BMHDA exhibits a desirably selective uptake pattern. An imaging study of a canine heart following [¹¹C] BMHDA injection one hour post-LAD ligation shows very high uptake in normal areas of the heart, and much lower uptake in the apex, the region in which the infarct is located.

The myocardial kinetics of BMHDA are evaluated in adult, fasted, human volunteers by positron tomography. Following attenuation measurements, volunteers receive between 1-5 mCi [¹¹C] BMHDA intravenously and serial images are recorded for 30 min. No changes in heart rate, blood pressure, ECG, or respiratory rate are observed. In all cases myocardial activity approaches a constant level within 3 min. and is constant for the remainder of the observation. The left ventricular myocardium is well delineated.

Beta-methyl-omega-(p-[¹³¹I] iodophenyl) tetradecanoic acid

A study of the biodistribution of [¹³¹I]-BMPTA in mice shows high levels of uptake in the heart and liver 5 minutes after injection, with high levels of radioactivity generally being maintained over the 30 minutes of the experiment. Uptake by the kidney peaks at 15 minutes, declining slightly 30 minutes after injection. Radioactivity in the lungs, blood, and in skeletal muscle is lower throughout the monitoring period.

Solutions of [¹³¹I]-BMPTA and, as a control, ²⁰¹Tl, are injected sequentially in a mongrel dog. After each injection, sequential images of the dog's heart are obtained using positron tomography. The imaging studies show longer retention of [¹³¹I]-BMPTA by the heart muscle, compared to retention of ²⁰¹Tl; clear images of the heart are obtained with [¹³¹I]-BMPTA as long as two hours after the injection, and activity in the heart remains essentially the same over the initial 60 minute period.

The relatively long retention times of the analogs of the invention in metabolizing tissue are believed to be due to a blocking of the beta-oxidation pathway. The substituted fatty acid analogs are taken up by healthy, metabolizing heart tissue in the same manner as are the corresponding fatty acids. In the analogs, however, the organic substitution interferes with beta-oxidation, the normal metabolic pathway of fatty acids in the heart, so that the analogs are partially metabolized and trapped in the myocardium, rendering them useful tools for imaging and metabolic studies.

In the normal course of mycardial fatty acid metabolism, a dehydrogenation reaction bonds coenzyme A to the fatty acid:

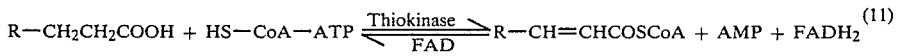

The resulting intermediate then undergoes hydration:

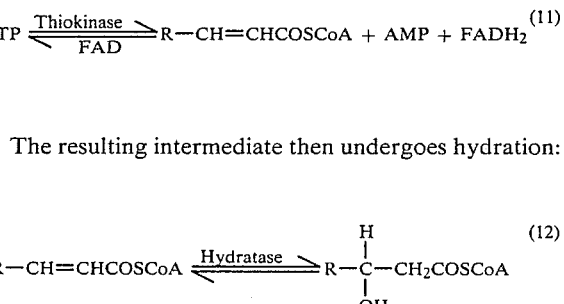

Reaction (12) is followed by oxidation to form the corresponding ketoacyl SCoA:

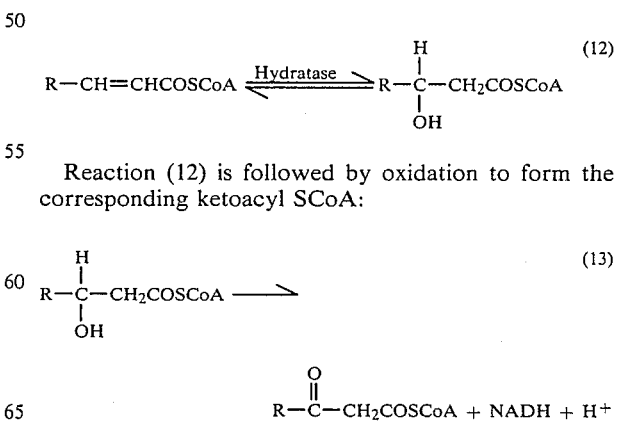

Acetyl CoA is then cleaved from the parent fatty acid to be metabolized by various pathways, while the fatty acid residue again undergoes the process outlined above, or is discharged from the tissue.

The substituents bonded at the C3 position of the analogs of the invention permit the coenzyme A bonding reaction (reaction (11)), but inhibit metabolism at the oxidation step (reaction (13)), preventing the formation of the beta-ketoacyl SCoA:

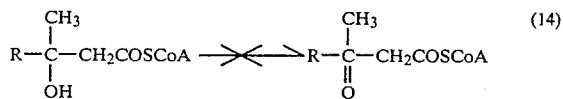

Metabolic inhibition at this point traps the analog in the metabolizing tissue and inactivates the beta-hydroxyacyl dehydrogenase to which the analog is bound, competitively inhibiting free fatty acid oxidation.

With a substituent at the C5, C7 or C9 position, the analog undergoes, respectively, 1, 2, or 3 cycles of the beta-oxidation pathway. When 2, 4, or 6 carbons are removed from the carboxylic end of the chain, the carbon to which the substituent is bonded is at the beta-position of a shortened fatty acid residue. This residue re-enters the beta-oxidation pathway, and beta-oxidation is blocked as outlined above.

In the omega-oxidation process, the omega-carbon of the fatty acid is carboxylated, after which it forms a complex with coenzyme A, and two carbons are removed from the fatty acid in the form of acetyl CoA, as in the beta-oxidation process outlined above. An organic substituent bonded to the antepenultimate carbon of the chain blocks omega-oxidation in a manner analagous to the beta-oxidation blocking action of the C3, C5, C7, and C9-substituted analogs of the invention.

The beta-oxidation-blocking action of the analogs of this invention suggests additional uses for them. For example, the analogs can be employed to study fatty acid metabolism in a given tissue by mixing one tissue sample homogenate with a C3 substituted analog of the invention and one with the corresponding fatty acid. The two metabolism rates can then be measured to compare the rate of normal metabolism, involving alpha-, beta-, and omega-oxidation, with the rate of metabolism under conditions in which beta-oxidation is inhibited. Similarly, an analog in which both omega- and beta-oxidation are blocked can be used to investigate the role of alpha-oxidation in fatty acid metabolism.

When attached to radical stable nitroxide, analogs of the invention can act as paramagnetic agents to enhance Nuclear Magnetic Resonance imaging.

Compounds of the invention, preferably those in which omega-oxidation, as well as beta-oxidation, is blocked, can be used in the therapy of diabetics. It has been suggested that excessive free fatty acid oxidation may be a key factor underlying decreased glucose tolerance in diabetes (Randle et al. (1966) Recent Prog. Horm. Res., 22, 1). Analogs of the invention can be administered to human patients (e.g., orally, intravenously, or parenterally) and, by decreasing the rate of fatty acid oxidation, can improve deficient muscle-glucose utilization in diabetics.

When used in diabetes therapy, analogs of the invention can be administered to a mammal in the dosage of 15 to 15,000 mcg/kg/day, preferably 1000 to 5000 mcg/kg/day.

OTHER EMBODIMENTS

Other embodiments are within the following claims. For example:

The chain length, as has been pointed out, can vary widely.

The nature and position of any radioactive label can also be varied. $^{11}C$ or $^{14}C$ is preferably placed at the carboxylic position for convenience in synthesis, although in theory this radioactive isotope could appear at any position on the chain, as well as on the substituent. Rather than using an isotope of carbon, a radioactive halogen isotope (e.g., $^{18}F$, $^{34m}Cl$, $^{75}Br$, $^{76}Br$, $^{77}Br$, $^{123}I$, or $^{131}I$) can be substituted at any position along the chain to provide a radioactive label. To prevent enzymatic dehalogenation, the halogen label can advantageously be included either in a substituted phenyl group or as a terminal transvinyl iodide group. In the beta-position, the halogenated phenyl group would serve both as radioactive label and as oxidation inhibitor.

Variation in the chain length of the analog, the nature and position of any radioactive label, and the nature and position of organic substituents will of course dictate concomitant variations in the synthesis of the analogs of the invention.

We claim:

1. A radioactively labeled analog of a fatty acid,
said analog being capable of being taken up by mammalian tissue,
said analog exhibiting an in vivo beta-oxidation rate below that of the corresponding radioactively labeled fatty acid.

2. The analog of claim 1, said analog having a chain of six or more carbon atoms and having bonded to it, at the C3, C5, C7, or C9 position, an organic substituent,
said substituent being effective to lower the rate of in vivo beta-oxidation of said analog, compared to that of the corresponding radioactively labeled fatty acid,
said analog having at least three carbon atoms in the straight chain to the left of the carbon atom to which said substituent is bonded.

3. The analog of claim 2, wherein said substituent is bonded to the C3 carbon atom.

4. The analog of claim 1, wherein said substituent causes said analog to be metabolically trapped in said tissue by permitting the occurrence of the first beta-oxidation step in which the carbon atom to which said substituent is bonded is beta to the carboxyl carbon atom, while preventing the cleaving off from said analog of the two carbon atoms to the right of the carbon atom to which said substituent is bonded.

5. The analog of claim 4 wherein said first step involves the bonding of coenzyme A to the carboxyl carbon atom, and
said cleaving off is prevented by the blocking by said substituent of the formation of a beta-ketoacyl SCoA intermediate.

6. The analog of claim 1, wherein said tissue is heart tissue.

7. The analog of claim 1, wherein said tissue is liver tissue.

8. The analog of claim 1, said analog being capable of emitting detectable positrons after being taken up by said tissue.

9. The analog of claim 1, said analog being capable of emitting detectable photons after being taken up by said tissue.

10. The analog of claim 1, wherein the carbon chain of said analog contains between 12 and 20 carbon atoms, inclusive.

11. The analog of claim 3, wherein the carbon chain of said analog contains between 6 and 11 carbon atoms, inclusive.

12. The analog of claim 1, wherein the carbon chain of said fatty acid is saturated.

13. The analog of claim 1, wherein the carbon chain of said fatty acid is unsaturated.

14. The analog of claim 1, wherein said organic substituent is an alkyl, aryl, or aralkyl group.

15. The analog of claim 1, wherein said substituent is an aryl group containing twelve or fewer carbon atoms.

16. The analog of claim 14, wherein said substituent is an alkyl group containing three or fewer carbon atoms.

17. The analog of claim 16, wherein said alkyl group is a methyl group.

18. The analog of claim 1, wherein said radioactive label is $^{11}C$ in the C1 position.

19. The analog of claim 1, wherein said radioactive label is $^{14}C$ in the C1 position.

20. The analog of claim 18, of the formula

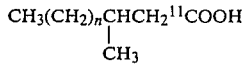

wherein n is an integer between 8 and 16, inclusive.

21. The analog of claim 20 wherein n is 13, said analog having the formula name [1-$^{11}C$] beta-methyl heptadecanoic acid.

22. The analog of claim 19, of the formula

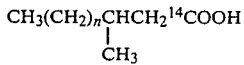

wherein n is an integer between 8 and 16, inclusive.

23. The analog of claim 22 wherein n is 13, said analog having the formula name [1-$^{14}C$] beta-methyl heptadecanoic acid.

24. The analog of claim 1, wherein said radioactive label is a radioactive isotope of a halogen.

25. The analog of claim 24 wherein said radioactive isotope of a halogen is $^{18}F$, $^{34m}Cl$, $^{75}Br$, $^{76}Br$, $^{77}Br$, $^{123}I$, or $^{131}I$.

26. The analog of claim 24, wherein said radioactive isotope of a halogen is bonded to a carbon atom on the straight chain of said analog.

27. The analog of claim 24, wherein said radioactive isotope of a halogen is bonded to an aryl group bonded to a carbon atom on the straight chain of said analog.

28. The analog of claim 27, wherein said radioactively labeled aryl group is bonded to the omega-carbon atom of said analog.

29. The analog of claim 28, wherein said aryl group is a phenyl group.

30. The analog of claim 15, wherein said aryl group has bonded to it a radioactive isotope of a halogen that serves as said radioactive label.

31. The analog of claim 29, of the formula

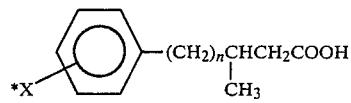

wherein *X is a radioactive isotope of a halogen and n is an integer between 9 and 17, inclusive.

32. The analog of claim 31, wherein *X is $^{131}I$ and n is 11, said analog having the formula name beta-methyl-omega-(p-[$^{131}I$] iodophenyl) tetradecanoic acid.

33. The analog of claim 31, wherein *X is $^{123}I$ and n is 11, said analog having the formula name beta-methyl-omega-(p-[$^{123}I$] iodophenyl) tetradecanoic acid.

34. The analog of claim 24, wherein said radioactive isotope of a halogen is bonded to a vinyl group bonded to a carbon atom on the straight chain of said analog.

35. The analog of claim 34, wherein said radioactively labeled vinyl group is bonded to the omega-carbon atom of said analog.

36. A fatty acid analog having a chain of six or more carbon atoms and being capable of being taken up by mammalian tissue,
the straight chain of said analog having bonded to it a first organic substituent at the C3, C5, C7, or C9 position,
said first substituent being effective to lower the rate of in vivo beta-oxidation of said analog, compared to that of the corresponding fatty acid,
the analog having at least three carbon atoms in the straight chain to the left of the carbon atom to which said first substituent is bonded,
said analog having, in addition to said first organic substituent, a second organic substituent bonded to the antepenultimate carbon atom of the chain,
said second organic substituent being effective to lower the rate of in vivo omega-oxidation of said analog, compared to that of the corresponding fatty acid.

37. The analog of claim 36, wherein said second organic substituent is an alkyl, aryl, or aralkyl group.

38. The analog of claim 36, wherein said second organic substituent is an aryl group containing twelve or fewer carbon atoms.

39. The analog of claim 37, wherein said second organic substituent is an alkyl group containing three or fewer carbons.

40. The analog of claim 39, wherein said second organic substituent is a methyl group.

41. The analog of claim 36, wherein said analog is radioactively labeled.

42. A method of reducing the rate of fatty acid metabolism in a human patient comprising administering to said patient a fatty acid metabolism rate-lowering amount of a fatty acid analog,
said analog having bonded to it, at the C3, C5, C7, or C9 position, an organic substituent,
said substituent being effective to lower the rate of in vivo beta-oxidation of said analog, compared to that of the corresponding fatty acid.

43. A method of reducing the rate of fatty acid metabolism in a human patient comprising administering to said patient a fatty acid metabolism rate-lowering amount of the analog of claim 36.

44. The method of claim 42 or claim 43 wherein said patient is suffering from diabetes mellitus.

* * * * *

UNITED STATES PATENT AND TRADEMARK OFFICE
CERTIFICATE OF CORRECTION

PATENT NO. : 4,524,059
DATED : June 18, 1985
INVENTOR(S) : David R. Elmaleh et al.

It is certified that error appears in the above-identified patent and that said Letters Patent are hereby corrected as shown below:

Column 1, delete lines 4-5 and insert:

--This invention was made with the Government support under Contract No. DE-AC02-76EV04115 awarded by the Department of Energy. The Government has certain rights in this invention.--

Column 4, line 23, " $\underline{\text{LiA/H/Ether}} \rightarrow CH_2(CH_2)_{13}CHCH_2OH$ " should be -- $\underline{\text{LiA/H/Ether}} \rightarrow CH_3(CH_2)_{13}CHCH_2OH$ --.

Signed and Sealed this

Thirty-first Day of December 1985

[SEAL]

Attest:

DONALD J. QUIGG

Attesting Officer

Commissioner of Patents and Trademarks